(12) United States Patent
Macke et al.

(10) Patent No.: US 10,729,558 B2
(45) Date of Patent: Aug. 4, 2020

(54) METHODS AND SYSTEMS FOR PATIENT-SPECIFIC ACETABULAR IMPLANTS

(71) Applicant: Zimmer, Inc., Warsaw, IN (US)

(72) Inventors: Jacob Macke, Warsaw, IN (US); Robert D. Krebs, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 12 days.

(21) Appl. No.: 16/040,878

(22) Filed: Jul. 20, 2018

(65) Prior Publication Data

US 2019/0053915 A1 Feb. 21, 2019

Related U.S. Application Data

(60) Provisional application No. 62/547,374, filed on Aug. 18, 2017.

(51) Int. Cl.
*A61F 2/46* (2006.01)
*A61B 34/10* (2016.01)
(Continued)

(52) U.S. Cl.
CPC .......... *A61F 2/4609* (2013.01); *A61B 34/10* (2016.02); *A61F 2/34* (2013.01); *A61F 2/4684* (2013.01); *A61B 17/175* (2013.01); *A61B 17/1746* (2013.01); *A61B 2017/568* (2013.01); *A61B 2034/102* (2016.02); *A61B 2034/105* (2016.02);
(Continued)

(58) Field of Classification Search
CPC ............... A61F 2/3094; A61F 2/30942; A61F 2002/30948; A61F 2/40; A61F 2/46; A61F 2/4609; A61F 2/4657; A61F 2/30; A61F 2002/3009; A61F 2002/30606; A61F 2002/30607; A61F 2002/30614;
(Continued)

(56) References Cited

U.S. PATENT DOCUMENTS 4,433,686 A * 2/1984 Charnley .................. A61F 2/34
606/81
10,245,163 B2 * 4/2019 Davenport ............ A61F 2/3609
(Continued)

FOREIGN PATENT DOCUMENTS

WO WO-2014159984 A1 10/2014

*Primary Examiner* — Alvin J Stewart
(74) *Attorney, Agent, or Firm* — Schwegman Lundberg & Woessner, P.A.

(57) ABSTRACT

Illustrative methods and systems for customizing a pre-manufactured acetabular shell to a specific patient are described herein. An illustrative method can include positioning a provisional shell at an acetabulum of the patient, the provisional shell having a plurality of selectable openings. The method further including marking, based on the assessing of the bone, a patient-matched hole location on a provisional liner that corresponds to one of the plurality of selectable openings in the provisional shell. With the provisional liner marked, the method can further include removing the provisional liner from the provisional shell and positioning the provisional liner in the pre-manufactured acetabular shell that is to be implanted in the patient. Using the provisional liner as a guide, the method can include forming a hole in the acetabular shell corresponding to the marked patient-matched hole location on the provisional liner.

20 Claims, 11 Drawing Sheets

(51) Int. Cl.
    *A61F 2/34*         (2006.01)
    *A61B 17/56*       (2006.01)
    *A61B 17/17*       (2006.01)
    *A61B 34/20*       (2016.01)
    *A61B 90/00*       (2016.01)

(52) U.S. Cl.
    CPC . *A61B 2034/108* (2016.02); *A61B 2034/2048* (2016.02); *A61B 2090/3937* (2016.02); *A61F 2002/3401* (2013.01); *A61F 2002/4687* (2013.01)

(58) Field of Classification Search
    CPC . A61F 2002/30616; A61F 2002/30617; A61B 17/17; A61B 17/1742; A61B 17/1746
    See application file for complete search history.

(56) References Cited

U.S. PATENT DOCUMENTS

| | | | |
|---|---|---|---|
| 2011/0093087 A1* | 4/2011 | Mcmahon | A61F 2/34 623/22.42 |
| 2013/0261632 A1* | 10/2013 | Livorsi | A61F 2/4609 606/91 |
| 2014/0100579 A1 | 4/2014 | Kelman et al. | |
| 2014/0208578 A1* | 7/2014 | Linderman | A61F 2/30756 29/592 |
| 2014/0330281 A1* | 11/2014 | Aghazadeh | A61B 17/60 606/102 |
| 2016/0074176 A1* | 3/2016 | Gillman | A61F 2/34 606/91 |
| 2016/0287395 A1* | 10/2016 | Khalili | A61F 2/30942 |
| 2018/0344466 A1* | 12/2018 | Lewallen | A61F 2/34 |

\* cited by examiner

METHODS AND SYSTEMS FOR PATIENT-SPECIFIC ACETABULAR IMPLANTS

CLAIM OF PRIORITY

This application claims the benefit of U.S. Provisional Patent Application Ser. No. 62/547,374, filed on Aug. 18, 2017, the benefit of priority of which is claimed hereby, and which is incorporated by reference herein in its entirety.

TECHNICAL FIELD

This document pertains generally, but not by way of limitation, to orthopedic devices, and, more particularly, to acetabular implants used in total hip arthroplasty.

BACKGROUND

A total hip arthroplasty (THA) procedure can be performed to repair a diseased or damaged hip joint and replace it with a hip prosthesis. Sometimes, as with any other mechanical device, a total hip replacement can be subject to various forms of mechanical or biological issues. When issues occur, a reoperation of the hip prosthesis can be necessary to resolve the issues. Such a reoperation of a THA is called a revision THA. This is usually done several years after the original implantation and is more common in patients who had the initial THA performed at a young age and the patient chose to have a very active physical lifestyle.

One of the challenges of a THA, including a revision THA is how to securely implant the hip prosthesis. In particular, it can be challenging to securely implant an acetabular shell of the prosthesis into the remaining bone of the patient, especially in the presence of poor bone quality or bone loss.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

Figure 1:
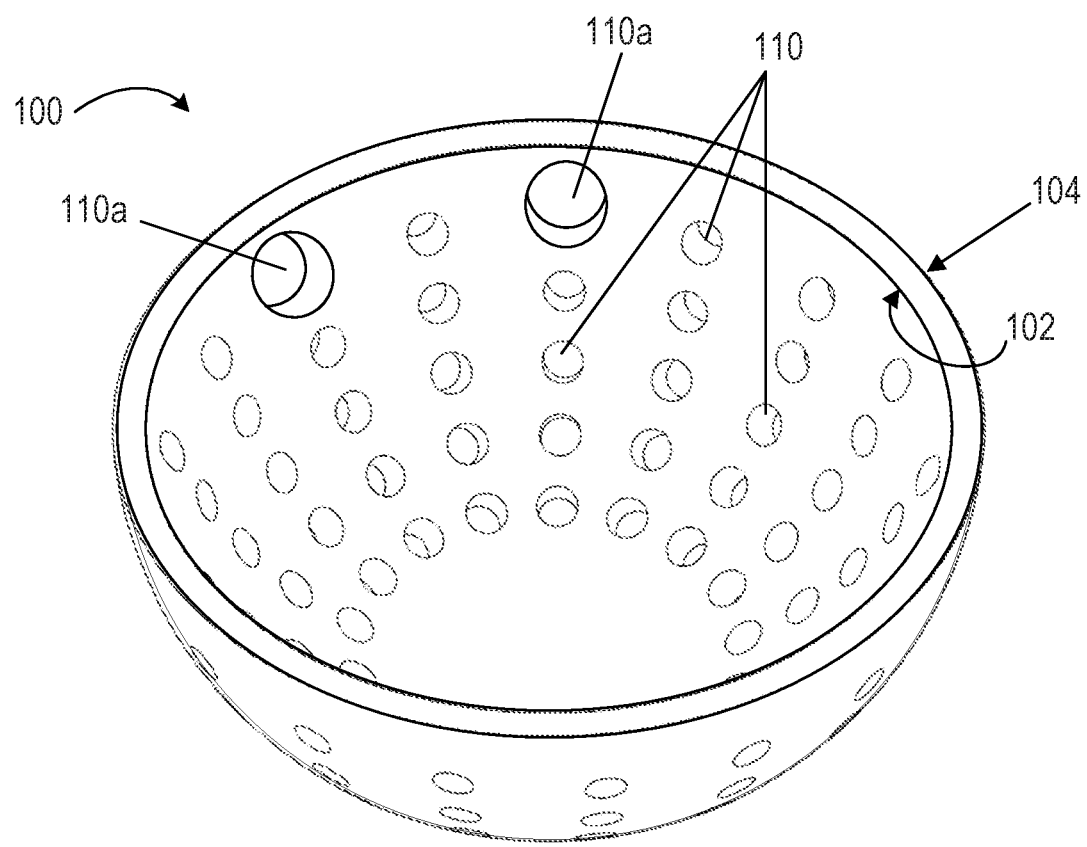
FIG. 1 is a perspective view of an illustrative provisional shell, in accordance with at least one example.

As discussed above, one of the challenges of a total hip arthroplasty (THA), including a revision THA, is how to securely implant the hip prosthesis. In particular it can be difficult to implant an acetabular revision shell of the prosthesis into the remaining bone of the patient, especially in the presence of poor bone quality or bone loss. Secure attachment of the shell to the bone reduces the risk of the shell migrating or loosening.

In addition, surgeons are limited to "off the shelf" (e.g., pre-manufactured) options having specified attachment locations. These off the shelf implants limit the surgeon's ability to match the implant to the specific needs and dimensions of the patient. The surgeon, selecting from these off the shelf options, is limited in finding a best match for fixing the shell to the available bone. The surgeon must match up the holes provided in the shell with the best locations in the bone. To do this, the surgeon must align, selecting from pre-formed holes manufactured into the shell, the best locations for securing the acetabular shell to the available bone. This method and system does not always produce the desired results.

To address these issues, improved implants and methods for supporting acetabular shells are described herein. The implants and methods can include modification options to increase the customizability of the implants to better match the anatomy of a patient. The implants have been found by the inventors to solve the problem of providing sufficient screw fixation in revision total hip arthroplasty (THA). The implants and methods can allow tailored fixation locations of the shell to the particular patient. In other words, the improved shells can provide individualized customization to the particular patient's anatomy in an "off the shelf" design. Some advantages of the improved shells can include: providing flexibility to the surgeon for selecting locations and forming fixation holes at the selected locations that match the native bone of a specific patient. In addition, when the surgeon creates only the specific holes needed to secure the acetabular shell, the amount of fixation area on the surface of the implant that faces the bone is maximized.

The implants and methods disclosed herein can improve surgeon options for attaching acetabular shells to an acetabulum of patient in a more customizable manner, and without the expense of a fully customized, patient-specific implant. Because the implants are more customizable to the patient over conventional implants, the quality of the implantation can be made more reliable. In some examples, the methods and systems described herein allow the surgeon to define the screw holes in the operating room, or preoperatively by analyzing image data, in order to patient-match the hole locations in the implant, to the patient's available bone. Analyzing the image data can include determining which of the plurality of openings in the provisional shell correspond to a preferred screw position.

The disclosure herein, while applied to implanting acetabular shells, can also be applied to implanting cage constructs. In addition, while the implants and methods can be described in relation to revision THA, the implants and methods can also be applied to non-revision, or first time THA surgeries and prosthesis.

As described herein, the term "hole" is generally associated with a screw hole, but it is not limited to holes that can only be used with screws. Other suitable types of fasteners besides screws can be inserted through the holes disclosed herein.

Figure 2:
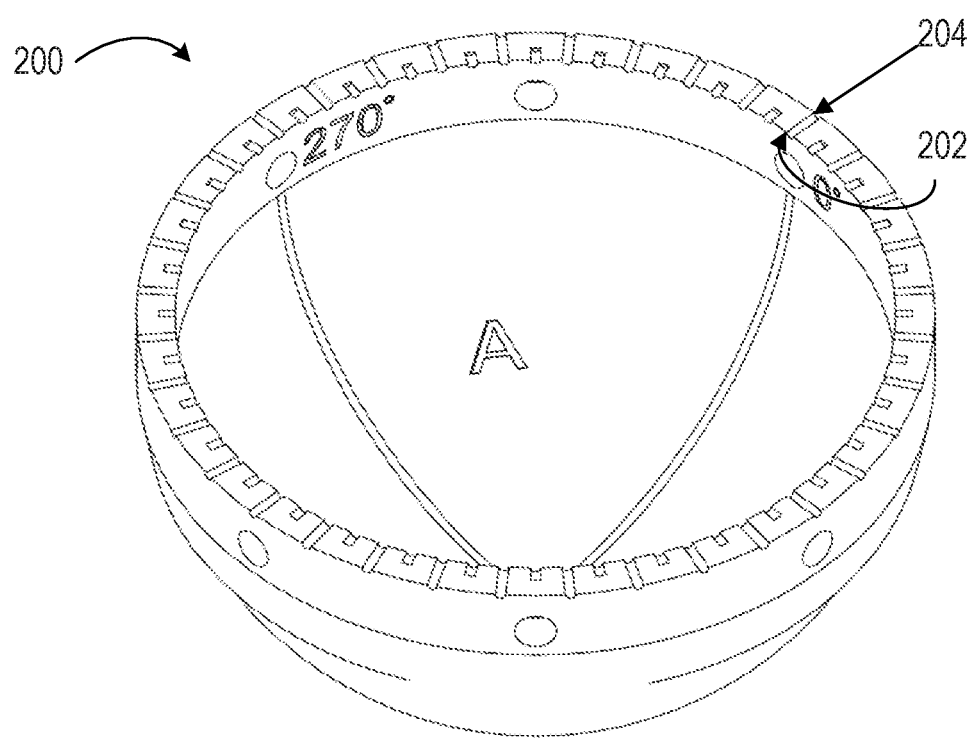
FIG. 2 is a perspective view of an illustrative provisional liner to be used with the illustrative provisional shell of FIG. 1, in accordance with at least one example.
Figure 3:
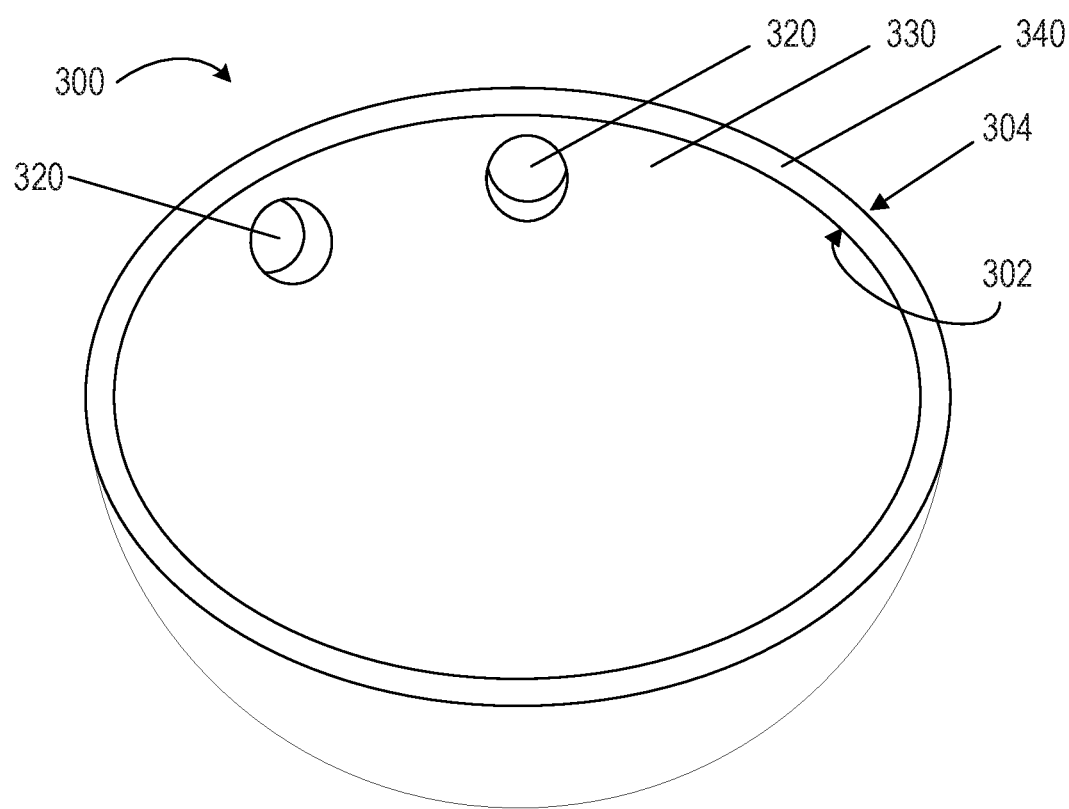
FIG. 3 is a perspective view of an illustrative acetabular shell that can be modified using the provisional liner of FIG. 2 prior to being implanted in a patient, in accordance with at least one example.

FIGS. 1-3 show an illustrative system for customizing an acetabular shell to a bone of a specific patient. The system can include a provisional shell 100 (FIG. 1), a provisional liner 200 (FIG. 2), and a customizable implant in the form of an acetabular shell 300 (FIG. 3). The provisional shell 100 and the provisional liner 200 can serve as tools in the customization process, while the acetabular shell 300 can be provided for actual implantation at the bone. In addition, tools such as a marking tool 60 (FIG. 6B) and a forming tool 800 (FIG. 8) can also be provided as part of the system.

FIG. 1 shows a perspective view of the provisional shell 100, in accordance with at least one example. The provisional shell 100 can have a first surface 102 and a second surface 104 opposite the first surface 102. The provisional shell 100 can be used as a template to determine the appropriate size acetabular shell to be implanted in the patient. A plurality of selectable openings 110 can extend through the provisional shell 100 from the first surface 102 to the second surface 104. The plurality of selectable openings 110 can be provided in the provisional shell 100 to aid a surgeon in determining where to form patient-matched holes in the acetabular shell 300 (FIG. 3). Creating patient-matched holes can improve the attachment of the acetabular shell to the patient's acetabulum where the patient has lost or poor quality bone in certain areas.

Because the provisional shell 100 is not generally intended for implantation but is used as a sizing and customization tool, more selectable openings 110 can be provided in the provisional shell 100 than can be realistically used for implanting the acetabular shell 300. For example, the selectable openings 110 can be provided in closer proximity to one another than would be provided in an acetabular shell to secure the acetabular shell to the patient. The selectable openings 110 can also be of a different size than would be provided in an acetabular shell to be implanted. The selectable openings can be provided in the pattern shown in FIG. 1, or any other suitable pattern. Another suitable pattern can include a staggered, radial pattern, such as can commonly be found in the arrangement of dimples on a golf ball.

In some examples, the plurality of selectable openings 110 in the provisional shell 100 can include one or more standard openings 110a that correspond in size, shape and location to pre-formed holes (e.g., 320, FIG. 3). The pre-formed holes 320 will be described in further detail with respect to FIG. 3. Depending on the acetabular shell 300 design that the provisional shell 100 is designed to complement, there may be a limited number of the standard openings 110a in the provisional shell, or no standard openings 110a in the provisional shell. The standard openings 110a can be a different size than other of the selectable openings 110. In some cases the standard openings 110a can be the same "full-sized" openings as the pre-formed holes 320 in the acetabular shell 300.

FIG. 2 shows a perspective view of the illustrative provisional liner 200 to be used with the illustrative provisional shell 100 of FIG. 1, in accordance with at least one example. The provisional liner 200 can have a first surface 202 and a second surface 204. The second surface 204 can be shaped and sized to correspond to the provisional shell 100 shape and to be positioned at the first surface 102 of the provisional shell 100 in a complementary form. As is shown and will be described later with reference to FIG. 6, an aspect of a method of using the system (100, 200, 300) can include positioning the provisional liner 200 proximate (e.g., adjacent, on) the first surface 102 of the provisional shell 100. In this aspect, to facilitate viewing the selectable openings 110 of the provisional shell 100 through the provisional liner 200, at least a portion of the provisional liner 200 can be formed of a transparent or semi-transparent polymer.

Figure 9:
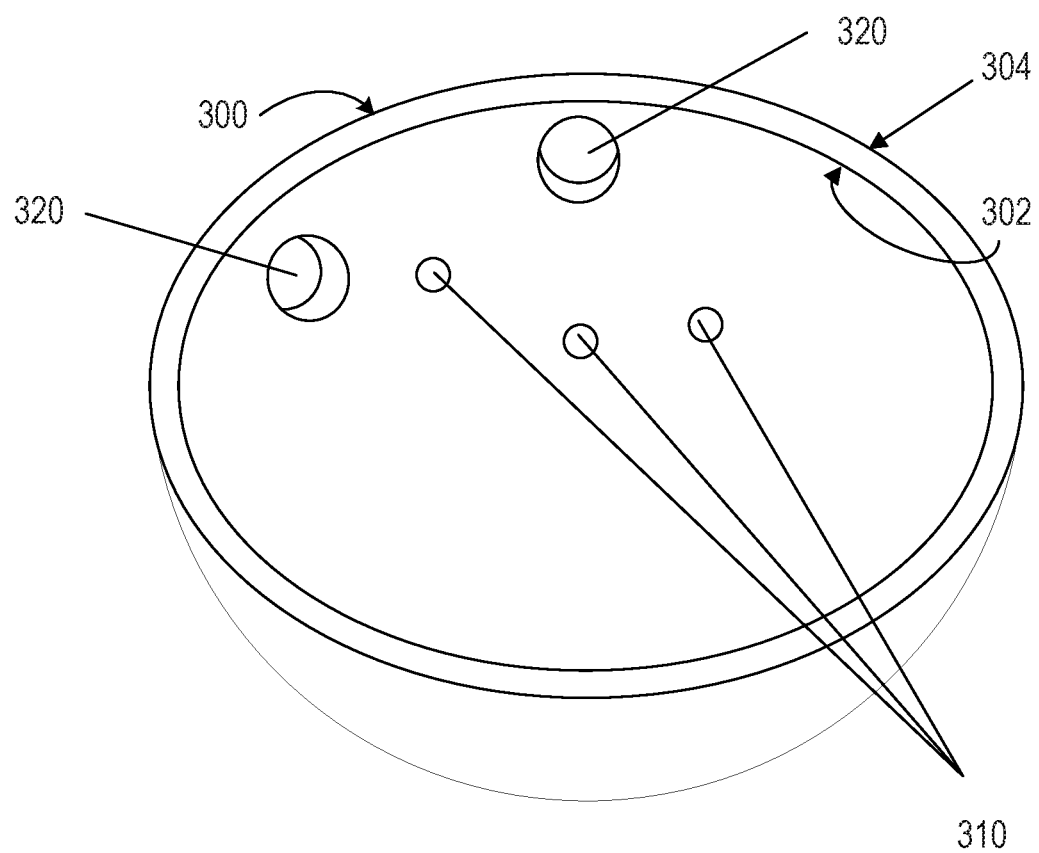
FIG. 9 is a perspective view of the acetabular shell of FIG. 3, including holes formed at the markings shown in FIG. 7, in accordance with at least one example.

In such an example, at least some or all of the plurality of selectable openings 110 of the provisional shell 100 can be viewed through the provisional liner 200 to allow the surgeon better visual access while creating a patient-matched hole marking(s) 210 on the provisional liner 200. The patient-matched hole markings 210 on the provisional liner 200 can correspond to patient-matched holes (e.g., 310 in FIG. 9) to be formed in the acetabular shell 300. The provisional liner 200 with patient-matched hole markings 210 can be used as a template to form patient-matched holes in an "off the shelf" (e.g., pre-manufactured) acetabular shell, such as the acetabular shell 300 of FIG. 3. The patient-matched holes 310 formed in the acetabular shell 300 are shown in FIG. 9.

FIG. 3 shows a perspective view of the illustrative acetabular shell 300 that can be customized. The acetabular shell 300 can be an "off the shelf" shell that can be customized to include patient-matched holes (e.g., 330, FIG. 9). The patient-matched holes 310 (FIG. 8) can be formed in the acetabular shell 300 using the patient-matched hole markings 210 on the provisional liner 200 as a guide. In contrast to the provisional shell 100 of FIG. 1, the acetabular shell 300 can be provided for actual implantation at the acetabulum 2, as opposed to being provided generally for provisional use (e.g., templating).

The acetabular shell 300 can be configured to receive the provisional liner 200 at the first surface 302. When placed in this location, adjacent the acetabular shell 300, the patient-matched hole markings 210 created on the provisional liner 200 by the surgeon can act as a guide to provide a location where a corresponding patient-matched hole location 310 (FIG. 9) can be formed in an acetabular shell 300.

Like the provisional shell 100, the acetabular shell 300 can have a first surface 302 opposite a second surface 304. In some examples, the illustrative acetabular shell 300 can be free of any pre-formed holes for securing the acetabular shell 300 to bone. In some examples, the acetabular shell 300 can include one or more pre-formed holes 320 for attaching the acetabular shell 300 to bone. If the one or more pre-formed holes 320 are provided, fewer pre-formed holes can be provided than what is needed to secure the acetabular shell 300 to the bone 1. Such pre-formed holes 320 can include, for example, holes that are generally used by a large population of patients and therefore do not need to be customized. As shown in the example of FIG. 3, the one or more pre-formed holes can be provided in a bearing surface portion 330 near a rim 340 of the acetabular shell 300.

Figure 4:
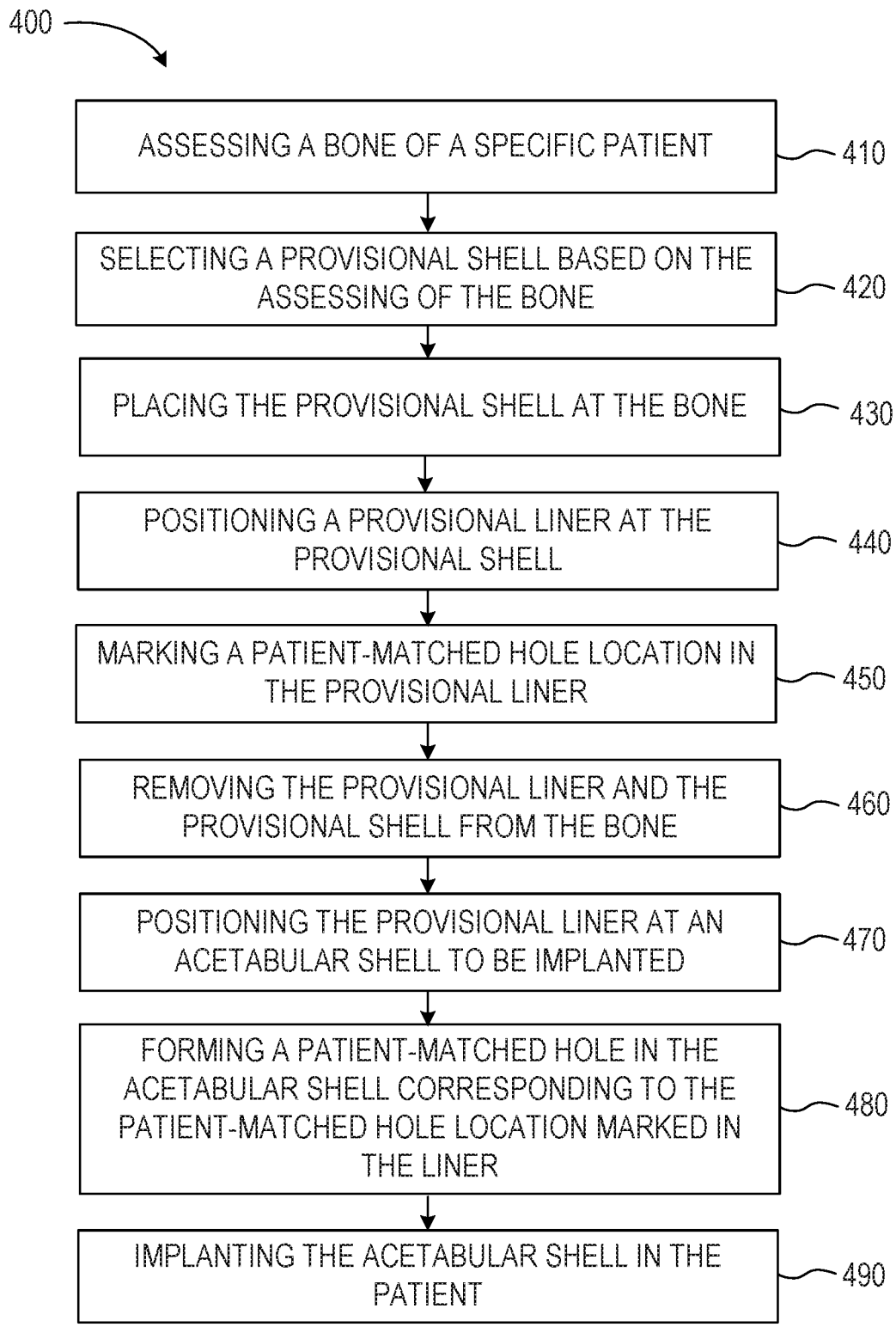
FIG. 4 is a flow chart illustrating a method of forming an acetabular shell using the system of FIGS. 1-3, and the process shown in FIGS. 5, 6A-6B and 7-9, in accordance with at least one illustrative example.

FIG. 4 shows a flow chart of an illustrative method 400 for forming an acetabular shell. The method 400 can be performed with a system such as, but not limited to, the system shown and described with reference to FIGS. 1-3. In addition to the flow chart of the method 400 shown in FIG. 4, aspects of the method are illustrated in FIGS. 5, 6A-6B and 7-9, in accordance with at least one example.

In aspects 410 and 420, the illustrative method 400 can include assessing a bone of a patient, and selecting a suitable provisional shell for the patient. The provisional shell 100 can be the same size, larger, or smaller than the acetabular shell 300.

Figure 5:
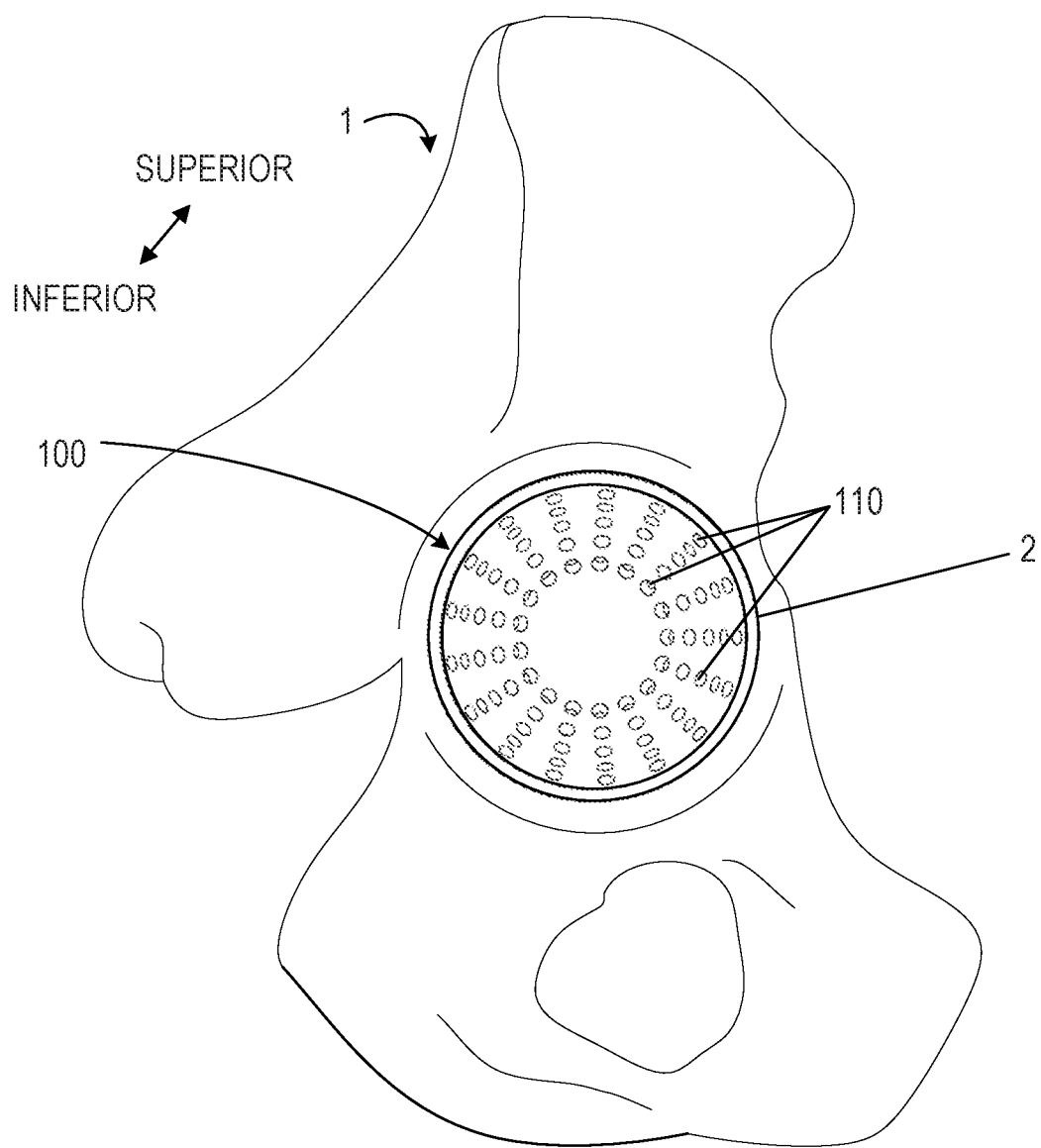
FIG. 5 is a top view of the illustrative provisional shell of FIG. 1 positioned at an acetabulum, in accordance with at least one example.

Aspect 430 can include positioning the provisional shell 100 at an acetabulum 2 of the bone 1. Aspect 430 is depicted in FIG. 5 which shows a top view of the illustrative provisional shell 100 of FIG. 1 positioned at an acetabulum 2.

Figure 8:
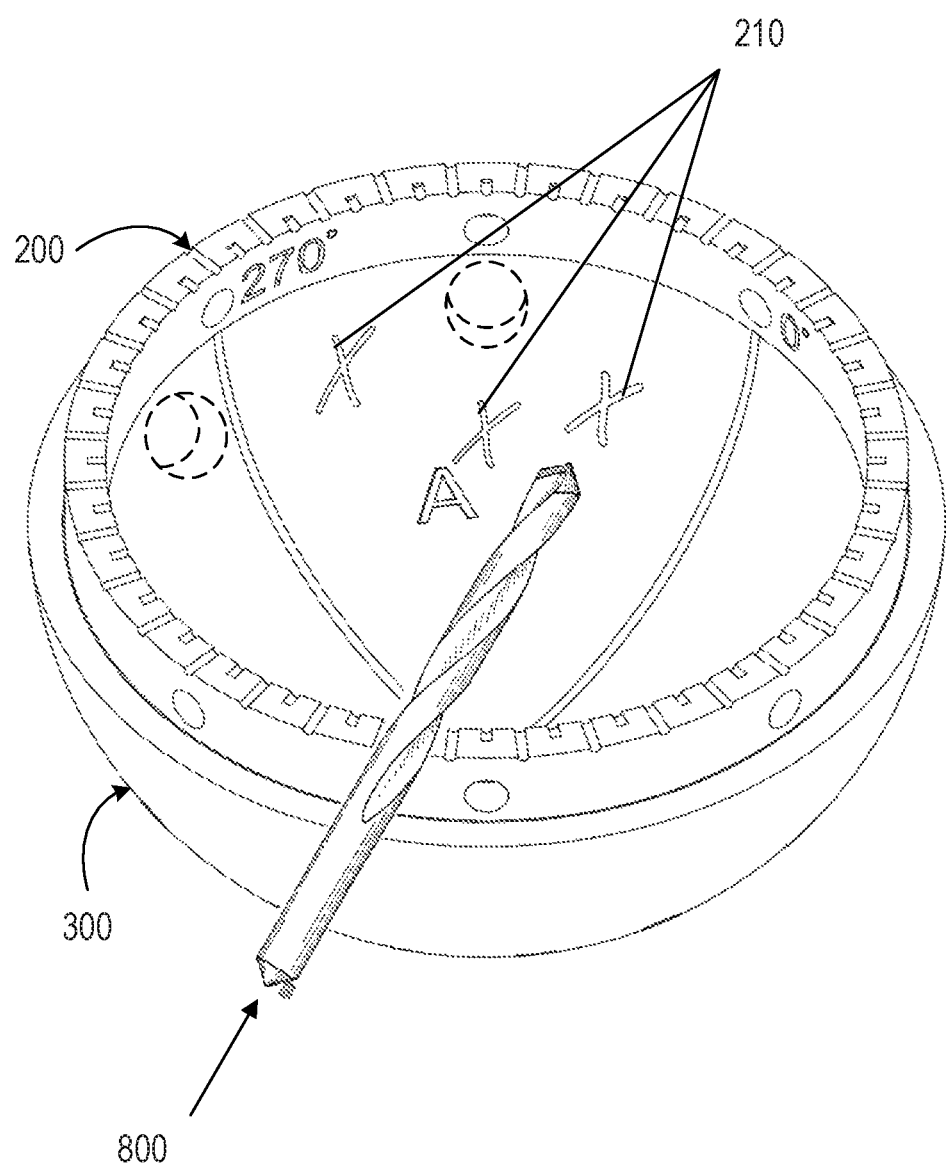
FIG. 8 is a perspective view of the provisional liner of FIG. 2 positioned in the acetabular shell of FIG. 3, in accordance with at least one example.

In aspect 430, when the provisional shell 100 is positioned at the acetabulum 2, the provisional shell 100 provides the surgeon the plurality of selectable openings 110 from which to choose locations for creating patient-matched holes 310 in the acetabular shell 300 (FIGS. 8 and 9). In some examples, the selectable openings 110 can be located in an arrangement reflecting the maximum density or minimum spacing between fasteners that can be supported by bone tissue. In some examples, the selectable openings 110 can be closer together than is suitable for implantation. For example, the selectable openings 110 can be provided in an arrangement closer together to provide the surgeon more options than are available in conventional acetabular shells, with the suggestion that two adjacent selectable openings 110 not be used in customizing the acetabular shell in order to maintain sufficient bone tissue.

Figure 6A:
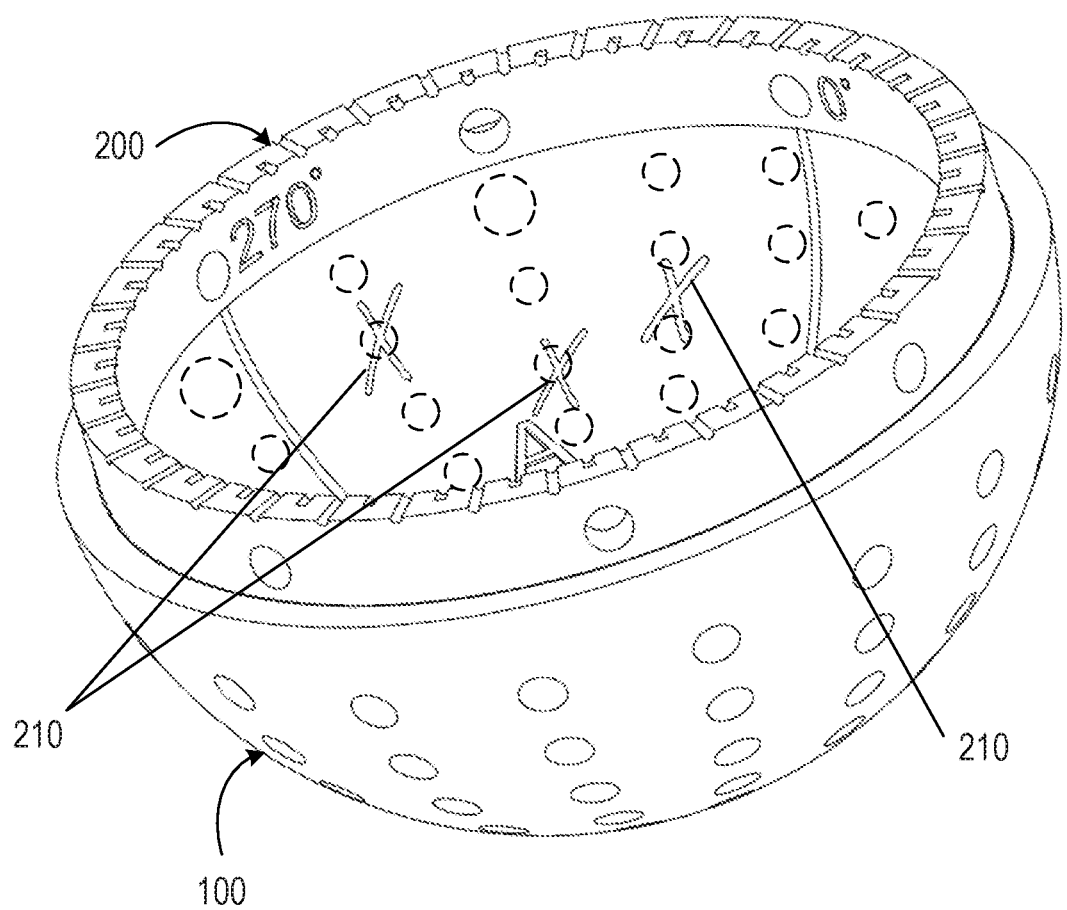
FIG. 6A is a perspective view of the provisional liner of FIG. 2 including markings, the provisional liner positioned in the provisional shell of FIG. 1, in accordance with at least one example.

Aspect 440, depicted in FIG. 6A, can include positioning the provisional liner 200 at the provisional shell 100. FIG. 6A is a perspective view of the provisional liner 200 of FIG. 2 positioned in the provisional shell 100 of FIG. 1, in accordance with at least one example. In order to show the relationship between the provisional liner 200 and the provisional shell 100, the hip bone is omitted in this view. In other words, in aspect 440 both the provisional shell 100 and the provisional liner 200 are placed at the acetabulum 2 adjacent one another with the provisional liner 200 placed in the provisional shell 100.

FIG. 6A also depicts aspect 450 which can include creating one or more patient-matched hole markings 210 on the provisional liner 200. Here, the provisional liner 200 is shown with the patient-matched hole markings 210 created by the surgeon to indicate locations for forming holes to customize the implantable acetabular shell 300. The surgeon can select and mark the patient-matched hole markings 210 according to the available bone in the specific patient. In some examples, the patient-matched hole markings 210 can be accomplished during a surgical procedure on the specific patient and based on the assessment of the bone in aspect 410. The assessment can include a physical visual and tactile assessment of the bone. In some examples, aspect 450 can also be accomplished anytime using image data instead of, or in addition to, any other assessment of the bone during the surgical procedure.

Figure 6B:
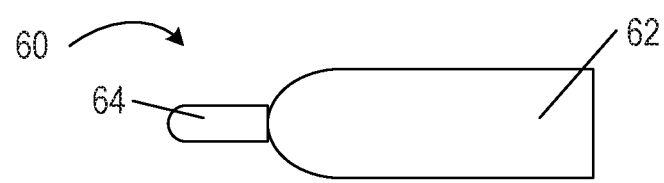
FIG. 6B is a side view of a marking tool for creating the markings shown in FIG. 5A.

FIG. 6B shows a marking tool 60 that can be used to create the patient-matched hole markings 210 shown in FIG. 6A. The marking tool 60 can have a handle 62 for holding the marking tool 60, and a tip 64 for dispensing the marking material. The marking tool 60 can be any suitable tool for permanently or temporarily marking the provisional liner 200, such as, but not limited to, a permanent marker, a wax pencil, or a mechanical or chemical etching tool.

Figure 7:
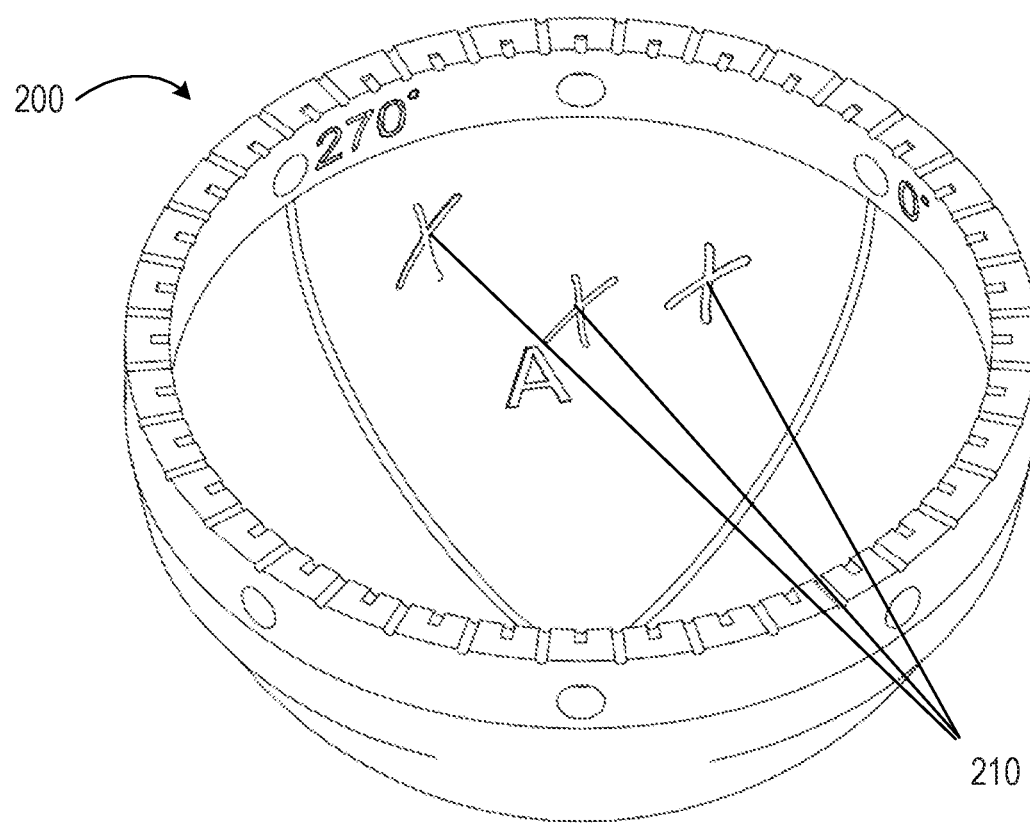
FIG. 7 is a perspective view of the provisional liner of FIG. 2 including the markings of FIG. 6A, with the provisional shell of FIG. 1 removed, in accordance with at least one example.

Aspect 460 includes removing the provisional liner 200 and the provisional shell 100 from the hip bone (e.g., 1, FIG. 5), and separating the provisional liner 200 from the provisional shell 100. To illustrate aspect 460, FIG. 7 shows a perspective view of the provisional liner 200 including the patient-matched hole markings 210 that were created in aspect 450 of FIG. 6A. The provisional liner 200 is then ready to be used as a template for customizing the acetabular shell 300 of FIG. 3 to the specific patient.

To customize the acetabular shell 300, aspect 470 can include positioning the provisional liner at the acetabular shell 300 to be implanted in preparation for forming patient-matched holes. FIG. 8 is a perspective view of the provisional liner 200 of FIG. 2 positioned in (e.g., nested with) the acetabular shell 300 of FIG. 3, in accordance with at least one example.

Aspect 480 can include forming a patient-matched hole(s) 310 in the acetabular shell 300 corresponding to the patient-matched hole marking 210 that was previously created on the provisional liner. FIG. 8 also shows a forming tool 800, such as a drill bit, that can be used to form the patient-matched hole through the acetabular shell 300, for example, when used with a drill. In some examples, the step of forming a patient-matched hole 310 can be performed during a surgical procedure to implant the acetabular shell 300 in the specific patient.

FIG. 9 is a perspective view of the acetabular shell 300 of FIG. 3, including the patient-matched holes 310 formed according to the patient-matched hole markings 210 on the provisional liner 200, in accordance with at least one example. Once the acetabular shell 300 is properly positioned at the bone 1 (FIG. 5), aspect 490 can include securing the acetabular shell 300 to the patient's acetabulum 2 (FIG. 5) using fasteners (e.g., screws, anchors, etc.) inserted through the patient-matched holes 310.

Figure 10:
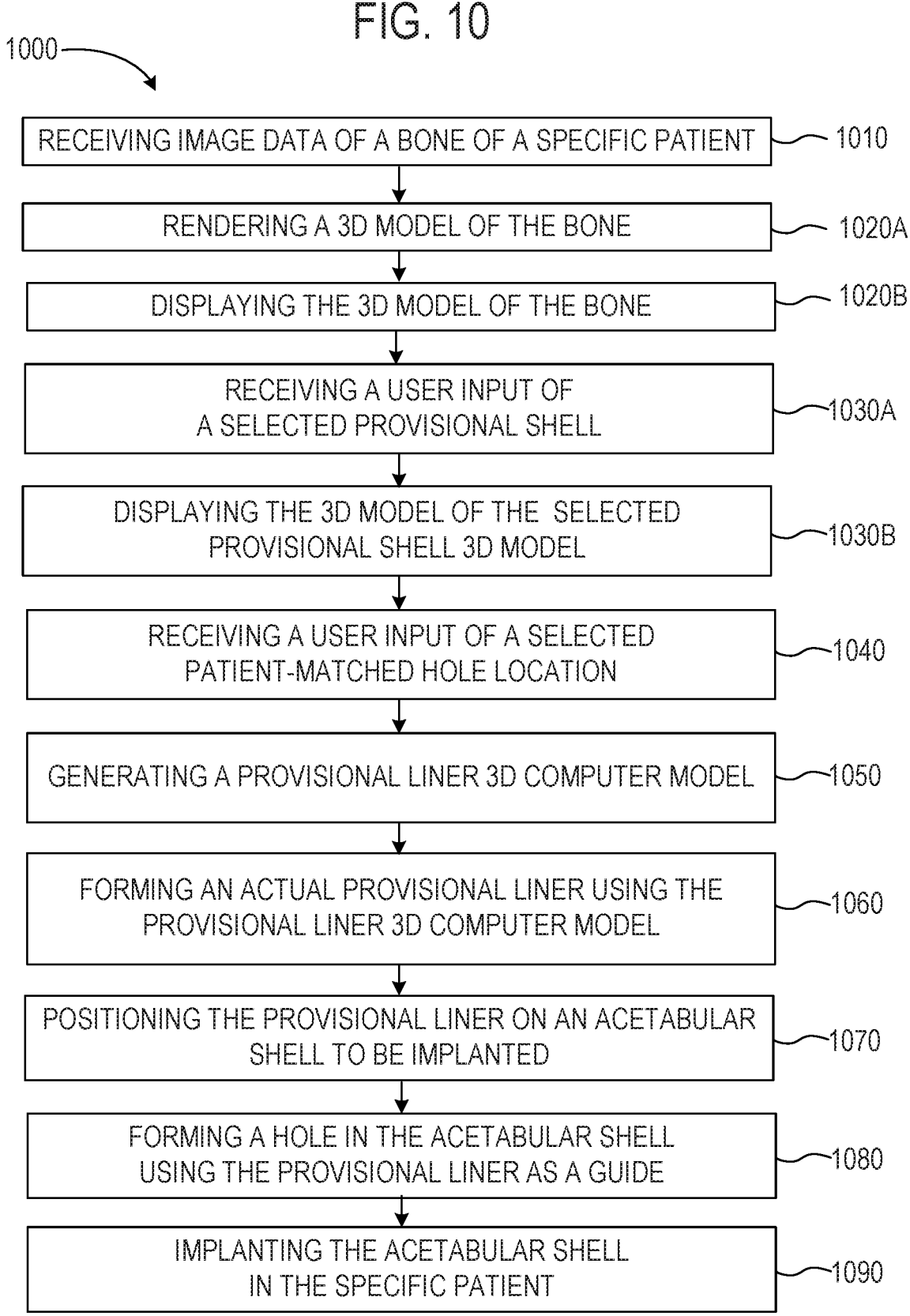
FIG. 10 is another illustrative method of forming an acetabular shell, incorporating the use of a machine, in accordance with at least one example.
Figure 11:
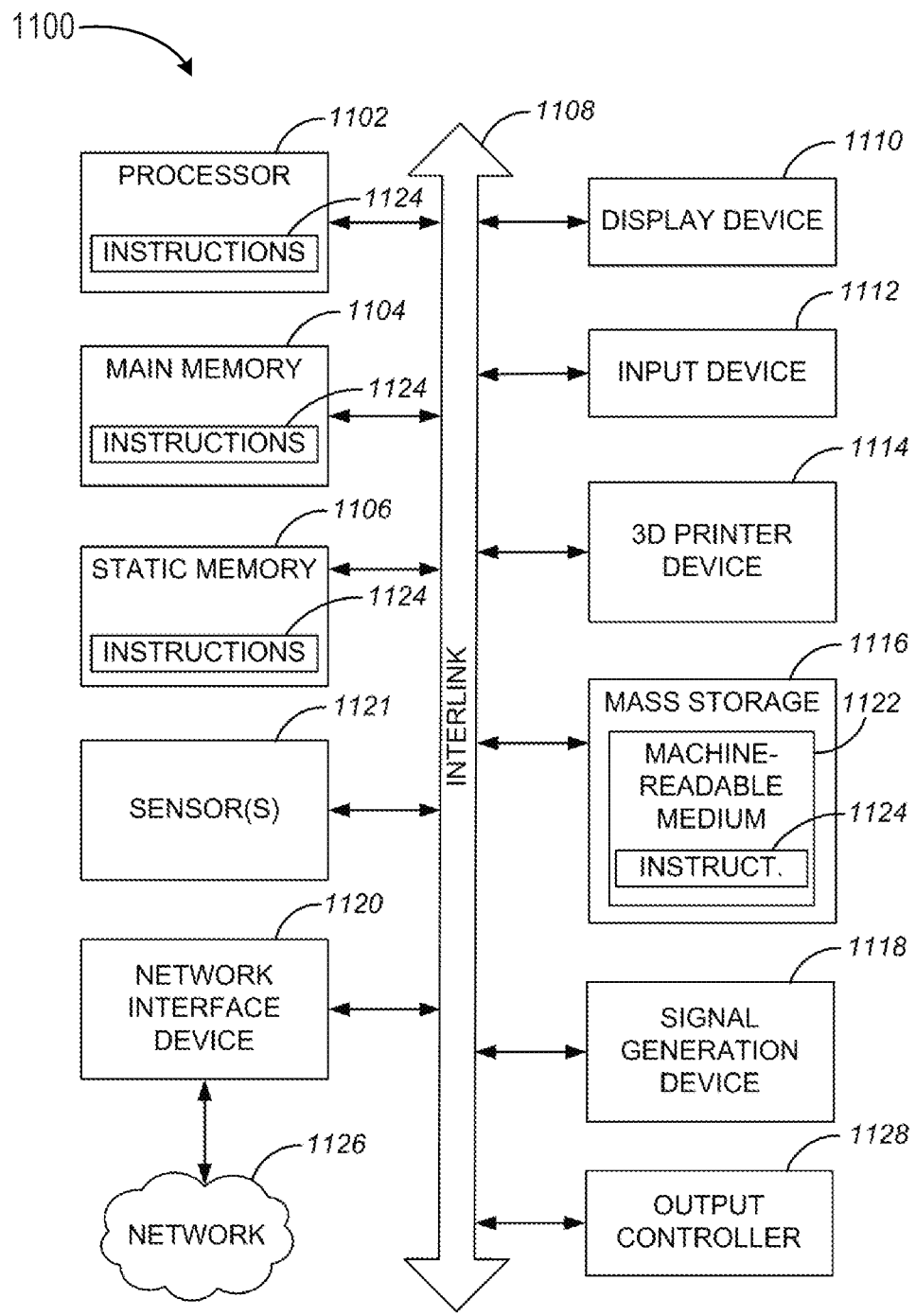
FIG. 11 is an illustrative system that can be used to perform the method of FIG. 10, in accordance with at least one illustrative example.

FIG. 10 shows another illustrative method 1000 for customizing acetabular shells to a specific patient. Method 1000 shares similar elements to method 400, but method 1000 can be practiced using a machine system 1100 (FIG. 11). The method 1000 can be performed using at least one non-transitory machine-readable medium including instructions (e.g., FIG. 11, 1124) for preparing a provisional liner (e.g., similar to 200, FIG. 2), which when executed by the machine 1100, cause the machine 1100 to perform aspects of the method 1000 outlined in the flow chart of FIG. 10.

Although the method 1000 is performed using a machine 1100, representations of the provisional shell 100, the provisional liner 200 and the acetabular shell 300 of the more manual system of FIGS. 1-3 and method 400 are applicable for the purpose of describing the method 1000. In contrast to the method 400, the physical components used in method 400 can be, in the method 1000, in the form of three-dimensional (3D) computer models that are manipulated on a user interface of a display.

With reference to FIG. 10, aspect 1010 can include receiving, at a processor (e.g., hardware module 1102 shown in FIG. 11), image data of a bone of a patient. Aspect 1020A can include rendering, using the processor 1102, a three-dimensional (3D) model of the bone using the image data. Aspect 1020B can include, displaying, on a display (e.g., on a user interface) operably coupled to the processor, the 3D model corresponding to the bone. Aspect 1030A can include receiving a user input of a selected provisional shell, while aspect 1030B can include displaying, on a display operably coupled to the processor 1102, the 3D computer model corresponding to the selected provisional shell (e.g., like 100, FIG. 1). In aspect 1030B, the provisional shell 3D model can include a plurality of selectable hole locations (e.g., like 110, FIG. 1). Aspect 1040 can include receiving, at the processor, a user input of a selected patient-matched hole location (e.g., like 310, FIG. 3). Aspect 1050 can include generating, using the processor 1102, a provisional liner 3D computer model including a guide opening (e.g., like 210, FIG. 2, except the markings can be actual holes) corresponding to the user's selected patient-matched hole location in the provisional shell.

Once the 3D model has been generated, aspect 1060 can include, either by hand, or by the machine 1100 or another machine, forming an actual, physical, provisional liner according to the 3D model. For example, the forming aspect 1060 can include printing, using a 3D printer, a provisional liner using the provisional liner 3D computer model. Other forming methods and forming machines besides 3D printing can be used to form the provisional liner.

Using the provisional liner formed in aspect 1060, aspect 1070 can include positioning the provisional liner on an acetabular shell (e.g., 300, FIG. 8) to be implanted in the patient, and forming a patient-matched hole in the acetabular shell using the guide opening (e.g., like patient matched hole marking 210, FIG. 7, but an actual hole) of the provisional liner to control a location of the patient-matched hole. Positioning in aspect 1070 can include nesting an outside surface of the provisional liner (e.g., second surface 204, FIG. 2) against an inside surface (e.g. first surface 302, FIG. 3) of the acetabular shell (e.g., 300, FIG. 8).

In some examples, the method can further include aspect 1080 of determining, with the processor 1102, a suggested patient-matched hole location and in aspect 1090, displaying the suggested patient-matched hole location in the bone. In some examples, displaying can also include displaying dimension information or bone characteristic information, such as bone density.

FIG. 11 is a general illustration of an example block diagram of a machine 1100 upon which any one or more of the methods (e.g., techniques) discussed herein can perform in accordance with some examples. In alternative examples, the machine 1100 can operate as a standalone device or can be connected (e.g., networked) to other machines. In a networked deployment, the machine 1100 can operate in the capacity of a server machine, a client machine, or both in server-client network environments. In some examples, the machine 1100 can act as a peer machine in peer-to-peer (P2P) (or other distributed) network environment. The machine 1100 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, can include, or can operate on, logic or a number of components, modules, or mechanisms. Modules are tangible entities (e.g., hardware) capable of performing specified operations when operating. A module includes hardware. In some examples, the hardware can be specifically configured to carry out a specific operation (e.g., hardwired). In some examples, the hardware can include configurable execution units (e.g., transistors, circuits, etc.) and a computer readable medium containing instructions, where the instructions configure the execution units to carry out a specific operation when in operation. The configuring can occur under the direction of the executions units or a loading mechanism. Accordingly, the execution units are communicatively coupled to the computer readable medium when the device is operating. In this example, the execution units can be a member of more than one module. For example, under operation, the execution units can be configured by a first set of instructions to implement a first module at one point in time and reconfigured by a second set of instructions to implement a second module.

Machine (e.g., computer system) 1100 can include a hardware processor 1102 (e.g., a central processing unit (CPU), a graphics processing unit (GPU), a hardware processor core, or any combination thereof), a main memory 1104 and a static memory 1106, some or all of which can communicate with each other via an interlink (e.g., bus) 1108. The machine 1100 can further include a display device 1110, an input device 1112 (e.g., a keyboard or other input), and a user interface (UI) navigation device 1114 (e.g., a mouse). In some examples, the display unit 1110, input device 1112 and UI navigation device 1114 can be a touch screen display. The machine 1100 can additionally include a storage device (e.g., drive unit) 1116, a signal generation device 1118 (e.g., a speaker), a network interface device 1120, and one or more sensors 1121, such as a global positioning system (GPS) sensor, compass, accelerometer, or other sensor. The machine 1100 can include an output controller 1128, such as a serial (e.g., universal serial bus (USB), parallel, or other wired or wireless (e.g., infrared (IR), near field communication (NFC), etc.) connection to communicate or control one or more peripheral devices (e.g., a 3D printer, card reader, etc.).

The storage device 1116 can include a machine readable medium 1122 that is non-transitory on which is stored one or more sets of data structures or instructions 1124 (e.g., software) embodying or utilized by any one or more of the techniques or functions described herein. The instructions 1124 can also reside, completely or at least partially, within the main memory 1104, within static memory 1106, or within the hardware processor 1102 during execution thereof by the machine 1100. In some examples, one or any combination of the hardware processor 1102, the main memory 1104, the static memory 1106, or the storage device 1116 can constitute machine readable media.

While the machine readable medium 1122 is illustrated as a single medium, the term "machine readable medium" can include a single medium or multiple media (e.g., a centralized or distributed database, or associated caches and servers) configured to store the one or more instructions 1124.

The term "machine readable medium" can include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples can include solid-state memories, and optical and magnetic media. Specific examples of machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1124 can further be transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In some examples, the network interface device 1120 can include one or more physical jacks (e.g., Ethernet, coaxial, or phone jacks) or one or more antennas to connect to the communications network 1126. In some examples, the network interface device 1120 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

The foregoing systems and devices, etc. are merely illustrative of the components, interconnections, communications, functions, etc. that can be employed in carrying out examples in accordance with this disclosure. Different types and combinations of sensor or other portable electronics devices, computers including clients and servers, implants, and other systems and devices can be employed in examples according to this disclosure.

In some examples, the implant 300 implanted according to the illustrative method 400 or the illustrative method 1000 can include a porous material that promotes boney ingrowth (e.g., supports boney ingrowth). In some examples, the implant 300 can be made partly or entirely of the porous material, partly or entirely of a solid material that is generally non-porous (e.g., solid metal, solid polymeric material), or a combination of both solid and porous materials.

To facilitate boney ingrowth, any of the implants described herein can be formed of a three-dimensional structure that promotes (e.g., supports) boney ingrowth. For example, a highly porous, three-dimensional metallic structure can be provided that incorporates one or more of a variety of biocompatible metals such as but not limited to titanium, a titanium alloy, cobalt chromium, cobalt chromium molybdenum, tantalum, a tantalum alloy, niobium, or alloys of tantalum and niobium with one another or with other metals. Such structures are particularly suited for contacting bone and/or soft tissue, and in this regard, can be useful as bone substitutes and other implants and implant components that are receptive to cell and tissue ingrowth, for example, by allowing boney tissue or other tissue to grow into the porous structure over time to enhance fixation (e.g., osseointegration) between the structure and surrounding bodily structures. According to certain examples of the present disclosure, an open porous metal structure, or a portion thereof, can have a bulk porosity as low as 55%, 65%, or 75% or as high as 80%, 85%, or 90%, or within any range defined between any pair of the foregoing values, and in this regard, such structures can provide lightweight, yet strong porous implants. Certain porous metal structures, despite having such high porosities, are capable of withstanding extreme mechanical loads at the time of implantation and over long periods of time, for example, where a highly porous, three-dimensional metallic structure is forcefully impacted and press fit into a bone, by itself or connected to another implant, and maintains its shape during impaction and following many months or years of service in the body. Such structures can be manufactured according to any suitable technique or process. An example of an open porous metal structure is produced using Trabecular Metal™ Technology available from Zimmer, Inc., of Warsaw, Ind. Trabecular Metal™ is a trademark of Zimmer, Inc. Such a material can be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

In some instances, a highly porous, three-dimensional metallic structure will be fabricated using a selective laser sintering (SLS) or other additive manufacturing-type process such as direct metal laser sintering or electron beam melting. In one example, a three-dimensional porous article is produced in layer-wise fashion from a laser-fusible powder, e.g., a single-component metal powder, which is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain examples, a laser selectively fuses powdered material by scanning cross-sections generated from a 3-D digital description of the article, e.g., from a CAD file or scan data, on the surface of a powder bed. Complex geometries can be created using such techniques, and in some instances, net shape and near net shape implants are constructed. In some examples, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as any of those disclosed herein.

Generally, a highly porous, three-dimensional metallic structure will include a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate can be in direct contact with the ligaments of the highly porous structure, for example, approximately 15%, 20%, or 25%, of the surface area of the substrate can be in direct contact with the ligaments of the highly porous structure.

A highly porous, three-dimensional metallic structure can be fabricated such that it comprises a variety of densities in order to selectively tailor the structure for particular orthopedic applications, for example, by matching the structure to surrounding natural tissue in order to provide an improved matrix for tissue ingrowth and mineralization. Such structures can be isotropic or anisotropic. In this regard, according to certain examples, an open porous metal structure can be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure can have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

In some examples, the porous metal structure can be a formed from a titanium alloy using an additive manufacturing process, such as with OsseoTi™, which is commercially available from Biomet Manufacturing, LLC (Warsaw, Ind., USA). Briefly, however, OsseoTi™ is highly biocompatible, has high corrosion resistance and includes a highly interconnected porous architecture that mimics the porous structure of human cancellous bone, which can enhance bone integration and in-growth. In one exemplary implementation, OsseoTi™ can include a porous construct with a porosity.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

VARIOUS NOTES AND EXAMPLES

To better illustrate the devices and methods disclosed herein, a non-limiting list of embodiments is provided herein.

Example 1 is a method for forming an acetabular shell, the method comprising: assessing a bone of a specific patient; selecting a provisional shell based on the assessing of the bone; positioning the provisional shell at the bone, the provisional shell having a plurality of openings; selecting a provisional liner; positioning the provisional liner in the provisional shell; marking, based on the assessing of the bone, a marked patient-matched hole location on the provisional liner corresponding to one of the plurality of openings in the provisional shell; removing the provisional liner from the provisional shell; removing the provisional shell from the bone; positioning the provisional liner in an acetabular shell to be implanted in the specific patient; and forming a patient-matched hole in the acetabular shell corresponding to the marked patient-matched hole location on the provisional liner.

In Example 2, the subject matter of Example 1 optionally includes positioning the acetabular shell at the bone; and securing the acetabular shell to the bone.

In Example 3, the subject matter of any one or more of Examples 1-2 optionally include wherein at least a portion of the provisional liner is transparent or semi-transparent.

In Example 4, the subject matter of any one or more of Examples 1-3 optionally include wherein assessing the bone of the specific patient is performed at the bone during a surgery.

In Example 5, the subject matter of any one or more of Examples 1-4 optionally include receiving image data of the bone, and wherein assessing the bone of the specific patient includes analyzing the image data.

In Example 6, the subject matter of Example 5 optionally includes wherein analyzing the image data includes, determining which of the plurality of openings in the provisional shell is a preferred screw position.

In Example 7, the subject matter of any one or more of Examples 1-6 optionally include wherein the acetabular shell is free of any pre-formed holes for securing the acetabular shell to the bone.

In Example 8, the subject matter of any one or more of Examples 1-7 optionally include wherein the acetabular shell includes a pre-formed hole, and wherein securing the acetabular shell to the bone includes securing the acetabular shell to the bone using the pre-formed hole and the patient-matched hole.

In Example 9, the subject matter of any one or more of Examples 1-8 optionally include wherein forming a hole in the acetabular shell includes drilling a hole in the acetabular shell.

In Example 10, the subject matter of any one or more of Examples 1-9 optionally include wherein forming a hole in the acetabular shell is performed during a surgery to implant the acetabular shell in the specific patient.

Example 11 is a system for customizing an acetabular shell to a bone of a specific patient, the system comprising: a provisional shell having a first surface and a second surface opposite the first surface, and a plurality of selectable openings extending from the first surface to the second surface; a provisional liner that corresponds to the provisional shell, wherein at least a portion of the provisional liner is transparent or semi-transparent, and wherein at least some of the plurality of selectable openings are viewable through the provisional liner when the provisional liner is placed adjacent the first surface; and an acetabular shell to be implanted in the bone, wherein the acetabular shell is configured to receive the provisional liner at the first surface, and wherein the provisional liner is configured to indicate a location for creating a hole in the acetabular shell.

In Example 12, the subject matter of Example 11 optionally includes wherein the provisional liner comprises a transparent or semi-transparent polymer.

In Example 13, the subject matter of any one or more of Examples 11-12 optionally include wherein the acetabular shell is free of any pre-formed holes for securing the acetabular shell to the bone.

In Example 14, the subject matter of any one or more of Examples 11-13 optionally include wherein the acetabular shell includes a pre-formed hole for attaching the acetabular shell to the bone.

In Example 15, the subject matter of any one or more of Examples 11-14 optionally include a marking tool configured to mark the provisional liner.

In Example 16, the subject matter of any one or more of Examples 11-15 optionally include a tool to form the hole through the acetabular shell.

Example 17 is a method of preparing a provisional liner three-dimensional (3D) computer model for customizing an acetabular shell to be implanted in a patient, the method comprising: receiving, at a processor, image data of a bone of a patient; rendering, using the processor, a three-dimensional (3D) model of the bone using the image data; displaying, on a display operably coupled to the processor, the 3D model of the bone; receiving, at the processor, a user input including a selected provisional shell; displaying, on the display, a provisional shell 3D model corresponding to the selected provisional shell, the provisional shell 3D model including a plurality of selectable hole locations; receiving, at the processor, a user input of a selected patient-matched hole location, selected from the plurality of selectable hole locations; and generating, using the processor, a provisional liner 3D computer model including a guide opening corresponding to the selected patient-matched hole location.

In Example 18, the subject matter of Example 17 optionally includes forming, using a forming machine, a provisional liner using the provisional liner 3D computer model.

In Example 19, the subject matter of any one or more of Examples 17-18 optionally includes printing, using a 3D printer, a provisional liner using the provisional liner 3D computer model.

In Example 20, the subject matter of any one or more of Examples 17-19 optionally include positioning the provisional liner on an acetabular shell to be implanted in the patient; and forming a hole in the acetabular shell using the guide opening of the provisional liner to control a location of the hole, the hole corresponding to the selected patient-matched hole location.

In Example 21, the subject matter of any one or more of Examples 17-20 optionally include wherein positioning the provisional liner includes nesting an outside surface of the provisional liner against an inside surface of the acetabular shell.

In Example 22, the subject matter of any one or more of Examples 17-21 optionally includes determining, with a processor, a suggested patient-matched hole location, and wherein displaying the 3D model of the bone includes displaying the suggested patient-matched hole location in the bone.

In Example 23, the subject matter of any one or more of Examples 17-22 optionally includes the 3D model of the bone including dimension information.

Example 24 is at least one non-transitory machine-readable medium including instructions for preparing a provisional liner three-dimensional (3D) computer model, which when executed by a machine, cause the machine to: receive image data of a bone of a patient; render a three-dimensional (3D) model of the bone using the image data; display, on a display, the 3D model of the bone; receive a user input including a selected provisional shell; display, on the display, a provisional shell 3D model corresponding to the selected provisional shell, the provisional shell 3D model including a plurality of selectable hole locations; receive a user input of a selection of a patient-matched hole location selected from the plurality of selectable hole locations; and generate a provisional liner 3D computer model including a guide opening corresponding to the selected patient-matched hole location.

In Example 25, the subject matter of Example 24 optionally includes instructions that cause the machine to: print, using a 3D printer, an actual provisional liner using the provisional liner 3D computer model.

In Example 26, the subject matter of any one or more of Examples 24-25 optionally include instructions that cause the machine to: form, using a forming machine, an actual provisional liner using the provisional liner 3D computer model.

In Example 27, the subject matter of Example 26 optionally includes instructions to form an acetabular shell, which when executed by the machine, cause the machine to: position the actual provisional liner on an acetabular shell, wherein the acetabular shell is to be implanted in the patient; and form a hole in the acetabular shell using the guide opening in the actual provisional liner to control the position of the hole in the acetabular shell, the hole corresponding to the selected patient-matched hole location.

Example 28 is a system for preparing a provisional liner, the system comprising: a processor coupled to memory including instructions for preparing the provisional liner, which when executed by the processor, cause the processor to: receive image data of a bone of a patient; render a three-dimensional (3D) model of the bone using the image data; display, on a display, the 3D model of the bone; receive a user input including a selected provisional shell; display, on the display, a provisional shell 3D model corresponding to the selected provisional shell, the provisional shell 3D model including a plurality of selectable hole locations; receive a user input of a selected patient-matched hole location selected from the plurality of selectable hole locations; and generate a provisional liner 3D computer model including a guide opening corresponding to the selected patient-matched hole location.

In Example 29, the subject matter of Example 28 optionally includes instructions that cause the processor to form, using a forming machine, an actual provisional liner using the 3D computer model.

In Example 30, the subject matter of any one or more of Examples 28-29 optionally includes instructions that cause the processor to print, using a 3D printer, an actual provisional liner using the provisional liner 3D computer model.

Example 31 is a system for preparing a provisional liner, the system comprising: a processor coupled to memory including instructions for preparing the provisional liner, which when executed by the processor, cause the processor to: receive image data of a bone of a patient; render a three-dimensional (3D) model of the bone using the image data; output the 3D model of the bone for display on a user interface of a display; receive a user input via the a user interface of the display, the user input including a selected provisional shell; output a provisional shell 3D model corresponding to the selected provisional shell for display on the user interface of the display, the provisional shell 3D model including a plurality of selectable hole locations; receive a user input, via the user interface of the display, of a selected patient-matched hole location selected from the plurality of selectable hole locations; and generate a provisional liner 3D computer model including a guide opening corresponding to the selected patient-matched hole location.

In Example 32, the subject matter of Example undefined includes, D computer model.

In Example 33, the subject matter of Example undefined includes, D computer model.

In Example 34, the subject matter of Example undefined includes, D model of the bone includes displaying the suggested patient-matched hole location in the bone.

Example 35 is at least one machine-readable medium including instructions that, when executed by processing circuitry, cause the processing circuitry to perform operations to implement of any of Examples 1-34.

Example 36 is an apparatus comprising means to implement of any of Examples 1-34.

Example 37 is a system to implement of any of Examples 1-34.

Example 38 is a method to implement of any of Examples 1-34.

What is claimed is:

1. A method for forming an acetabular shell, the method comprising:
    assessing a bone of a specific patient;
    selecting a provisional shell based on the assessing of the bone;
    positioning the provisional shell at the bone, the provisional shell having a plurality of openings;
    selecting a provisional liner;
    positioning the provisional liner in the provisional shell;
    marking, based on the assessing of the bone, a marked patient-matched hole location on the provisional liner corresponding to one of the plurality of openings in the provisional shell;
    removing the provisional liner from the provisional shell;
    removing the provisional shell from the bone;
    positioning the provisional liner in an acetabular shell to be implanted in the specific patient; and
    forming a patient-matched hole in the acetabular shell corresponding to the marked patient- matched hole location on the provisional liner.

2. The method of claim 1, further comprising:
    positioning the acetabular shell at the bone; and
    securing the acetabular shell to the bone.

3. The method of claim 1, wherein at least a portion of the provisional liner is transparent or semi-transparent.

4. The method of claim 1, wherein assessing the bone of the specific patient is performed at the bone during a surgery.

5. The method of claim 1, further comprising receiving image data of the bone, and wherein assessing the bone of the specific patient includes analyzing the image data.

6. The method of claim 5, wherein analyzing the image data includes, determining which of the plurality of openings in the provisional shell is a preferred screw position.

7. The method of claim 1, wherein the acetabular shell is free of any pre-formed holes for securing the acetabular shell to the bone.

8. The method of claim wherein the acetabular shell includes a pre-formed hole, and wherein securing the acetabular shell to the bone includes securing the acetabular shell to the bone using the pre-formed hole and the patient-matched hole.

9. The method of claim 1, wherein forming a hole in the acetabular shell includes drilling a hole in the acetabular shell.

10. The method of claim 1, wherein forming a hole in the acetabular shell is performed during a surgery to implant the acetabular shell in the specific patient.

11. A system for customizing an acetabular shell to a bone of a specific patient, the system comprising:
    a provisional shell having a first surface and a second surface opposite the first surface, and a plurality of selectable openings extending from the first surface to the second surface;
    a provisional liner that corresponds to the provisional shell, wherein at least a portion of the provisional liner is transparent or semi-transparent, and wherein at least some of the plurality of selectable openings are viewable through the provisional liner when the provisional liner is placed adjacent the first surface; and
    an acetabular shell to be implanted in the bone, wherein the acetabular shell is configured to receive the provisional liner at the first surface, and wherein the provisional liner is configured to indicate a location for creating a hole in the acetabular shell.

12. The system of claim 11, wherein the provisional liner comprises a transparent or semi-transparent polymer.

13. The system of claim 11, wherein the acetabular shell is free of any pre-formed holes for securing the acetabular shell to the bone.

14. The system of claim 11, wherein the acetabular shell includes a pre-formed hole for attaching the acetabular shell to the bone.

15. The system of claim 11 further comprising a marking tool configured to mark the provisional liner.

16. The system of claim 11, further comprising a tool to form the hole through the acetabular shell.

17. A system for preparing a provisional liner, the system comprising:
  a processor coupled to memory including instructions for preparing the provisional liner, which when executed by the processor, cause the processor to:
  receive image data of a bone of a patient;
  render a three-dimensional (3D) model of the bone using the image data;
  output the 3D model of the bone for display on a user interface of a display;
  receive a user input via the the user interface of the display, the user input including a selected provisional shell;
  output a provisional shell 3D model corresponding to the selected provisional shell for display on the user interface of the display, the provisional shell 3D model including a plurality of selectable hole locations;
  receive a user input, via the user interface of the display, of a selected patient-matched hole location selected from the plurality of selectable hole locations; and
  generate a provisional liner 3D computer model including a guide opening corresponding to the selected patient-matched hole location.

18. The system of claim 17, wherein the instructions further cause the processor to output the provisional liner 3D computer model to a forming machine to form an actual provisional liner using the provisional liner 3D computer model.

19. The system of claim 17, wherein the instructions further cause the processor to output the provisional liner 3D computer model to a 3D printer to print an actual provisional liner using the provisional liner 3D computer model.

20. The system of claim 17, wherein the instructions further cause the processor to determine a suggested patient-matched hole location, and wherein displaying the 3D model of the bone includes displaying the suggested patient-matched hole location in the bone.

* * * * *

UNITED STATES PATENT AND TRADEMARK OFFICE
CERTIFICATE OF CORRECTION

PATENT NO. : 10,729,558 B2
APPLICATION NO. : 16/040878
DATED : August 4, 2020
INVENTOR(S) : Macke et al.

Page 1 of 1

It is certified that error appears in the above-identified patent and that said Letters Patent is hereby corrected as shown below:

In the Claims

In Column 16, Line 28, in Claim 8, delete "claim" and insert --claim 1,-- therefor Signed and Sealed this
Sixth Day of October, 2020

Andrei Iancu
*Director of the United States Patent and Trademark Office*